United States Patent
Takahashi et al.

(10) Patent No.: US 7,626,172 B2
(45) Date of Patent: Dec. 1, 2009

(54) NUCLEAR MEDICAL DIAGNOSIS APPARATUS

(75) Inventors: Isao Takahashi, Hitachi (JP); Kazuma Yokoi, Hitachi (JP); Tsuneaki Kawaguchi, Kashiwa (JP); Katsutoshi Tsuchiya, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 12/039,270

(22) Filed: Feb. 28, 2008

(65) Prior Publication Data

US 2008/0310580 A1    Dec. 18, 2008

(30) Foreign Application Priority Data

Jun. 15, 2007  (JP) .............................. 2007-158554

(51) Int. Cl.
*G01T 1/161* (2006.01)

(52) U.S. Cl. ................................................ 250/363.07
(58) Field of Classification Search ............. 250/363.07
See application file for complete search history.

(56) References Cited

U.S. PATENT DOCUMENTS

| | | | |
|---|---|---|---|
| 3,862,425 A | | 1/1975 | Myers |
| 5,371,672 A | * | 12/1994 | Motomura et al. .......... 600/431 |
| 5,742,056 A | | 4/1998 | Valentino et al. |
| 6,175,118 B1 | * | 1/2001 | Takayama et al. ........... 250/369 |

2002/0121603 A1    9/2002  Wong et al.

FOREIGN PATENT DOCUMENTS

| JP | 7-128450 | 5/1995 |
|---|---|---|
| JP | 2005-17142 | 1/2005 |
| JP | 2005-109269 | 4/2005 |

OTHER PUBLICATIONS

Ichihara, et al., "Compton Scatter Compensation Using the Triple-Energy Window Method for Single-and Dual-Isotope SPECT" The Journal of Nuclear Medicine, vol. 34, No. 12, pp. 2216-2221, Dec. 1993.

* cited by examiner

*Primary Examiner*—David P Porta
*Assistant Examiner*—Shun Lee
(74) *Attorney, Agent, or Firm*—Brundidge & Stanger, P.C.

(57) ABSTRACT

A nuclear medial diagnosis apparatus is used for performing diagnosis by administering a medicine marked with a radioactive isotope into an examinee and by using an image obtained by detecting gamma rays emitted from a particular organ or tumor where the medicine is accumulated. An image (an image created by an image creation unit) is created by a signal (a signal as an output from a radiation detector) corresponding to the energy of the gamma ray detected by a radiation detector. The image includes a contamination component attributed to gamma scattering in the radiation detector. An image correction operation unit performs a convolution operation to obtain a contamination image. The contamination image is subtracted by a corrected image creation unit. Thus, it is possible to prevent image degradation by the gamma ray scattering in the radiation detector.

8 Claims, 8 Drawing Sheets

FIG. 2A

| 0 | 0 | 0 | 0 | 0 |
|---|---|---|---|---|
| 0 | 0 | 0 | 0 | 0 |
| 0 | 0 | 100 | 0 | 0 |
| 0 | 0 | 0 | 0 | 0 |
| 0 | 0 | 0 | 0 | 0 |

FIG. 2B

| 0 | 1 |   | 1 | 0 |
|---|---|---|---|---|
| 1 | 5 | 10 | 5 | 1 |
|   | 10 | 0 | 10 |   |
| 1 | 5 | 10 | 5 | 1 |
| 0 | 1 |   | 1 | 0 |

| 0 | 1 | 2 | 1 | 0 |
|---|---|---|---|---|
| 1 | 5 | 10 | 5 | 1 |
| 2 | 10 | 0 | 10 | 2 |
| 1 | 5 | 10 | 5 | 1 |
| 0 | 1 | 2 | 1 | 0 |

FIG. 6B

| 1 | 5 | 10 | 5 | 1 |
|---|---|---|---|---|
| 2 | 10 | 0 | 10 | 2 |
| 1 | 5 | 10 | 5 | 1 |
| 0 | 1 | 2 | 1 | 0 |
| 0 | 0 | 0 | 0 | 0 |

FIG. 6C

| 0 | 0 | 0 | 0 | 0 |
|---|---|---|---|---|
| 0 | 1 | 2 | 1 | 0 |
| 1 | 5 | 10 | 5 | 1 |
| 2 | 10 | 0 | 10 | 2 |
| 1 | 5 | 10 | 5 | 1 |

DETECTION SIGNAL :

NUCLEAR MEDICAL DIAGNOSIS APPARATUS

BACKGROUND OF THE INVENTION

The present invention relates to a nuclear medical diagnosis apparatus and in particular, to an image processing in a gamma camera and a single photon emission computed tomography (SPECT) configured by using the gamma camera.

In the nuclear medical diagnosis using a nuclear medical diagnosis apparatus, a medicine marked by a radioactive isotope is applied to an examinee. When the medicine is accumulated in a particular organ or a tumor, a gamma ray is emitted from there. By detecting the gamma ray by a radiation detector (hereinafter, referred to simply as a detector), it is possible to obtain an image based on the medicine distribution.

Moreover, by using medicines of different characteristics, it is possible to perform more accurate nuclear medical diagnosis. For example, by using $^{99m}$Tc-MIBI capable of obtaining information on the myocardial perfusion and the regional wall motion and $^{123}$I-BMIPP capable of obtaining myocardial metabolism information to perform two-nuclide imaging, it is possible to perform more preferable heart function diagnosis.

Moreover, it is advantageous to use one nuclide emitting gamma rays of a plurality of energies such as $^{201}$Tl, because it is possible to simultaneously observe two accumulation portions (portions where the administrated medicine is accumulated), i.e., only the vicinity of the body skin by the gamma ray having a low energy and a comparatively deep region by the gamma ray having a high energy. Hereinafter, a multiple nuclide imaging and imaging using a nuclide emitting gamma rays of a plurality of energies will be referred to as "multiple nuclide imaging and the like".

Figure 7:
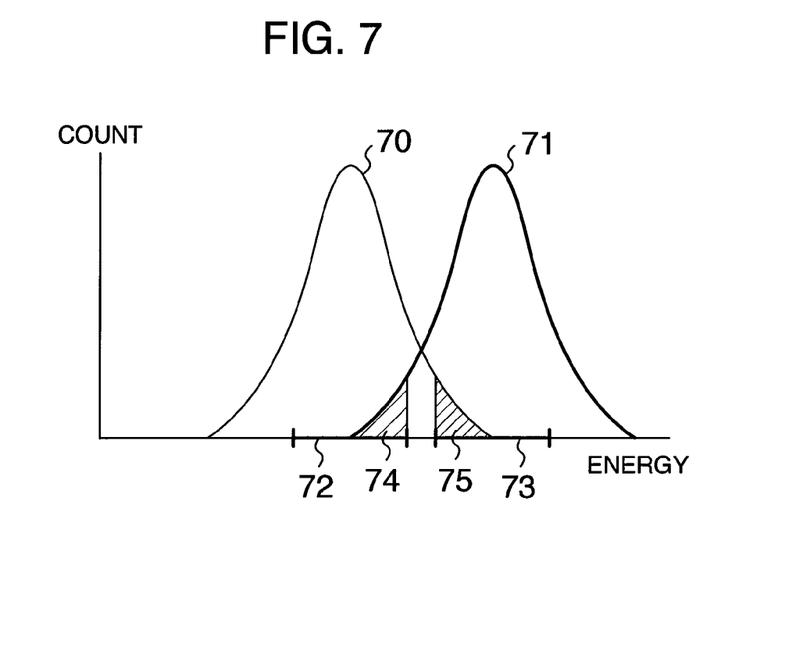
FIG. 7 shows an energy spectrum of the detector obtained upon two-nuclide imaging, which expresses contamination attributed to insufficient energy resolution.

In the case of the multiple nuclide imaging and the like, contamination of an image corresponding to the gamma ray of a predetermined energy may be caused by a gamma ray of a different energy from the predetermined energy and correction should be made. It should be noted that the contamination means an image corresponding to a gamma ray of other energy than a predetermined energy coming into the image corresponding to the gamma ray of the predetermined energy, which causes degradation of the image corresponding to the predetermined energy. One of the causes which causes the contamination is that the detector does not have an ideal high energy resolution. For example, the gamma ray of 140 keV emitted from $^{99m}$Tc has energy (photo peak) near to that of the gamma ray of 159 keV emitted from $^{123}$I and accordingly, if the energy resolution is insufficient, as shown in FIG. 7, bottoms of peaks 70 and 71 are overlapped on the energy spectrum. To solve this problem, conventionally the effect of the contamination is estimated by quantitatively evaluating, in advance, a contamination component 75 (74) of a total absorption peak 70 (71) of the gamma ray emitted from $^{99m}$Tc, in a predetermined range (energy window 73) corresponding to the energy of the gamma ray emitted from $^{123}$I for example, in case of an imaging only of the image corresponding to the gamma ray of 140 keV emitted from $^{99m}$Tc (gamma ray emitted from $^{123}$I, in a predetermined range (energy window 72) corresponding to the energy of the gamma ray emitted from $^{99m}$Tc, for example, in case of an imaging only of the image corresponding to the gamma ray of 140 keV emitted from $^{123}$I).

Another factor of the contamination is scattering of the gamma ray in an examinee. In the nuclear medical diagnosis apparatus, distribution of the position where the gamma ray is generated is imaged according to the gamma ray coming from directly from the accumulation portion of the administered medicine. On the other hand, when the gamma ray is scattered in the examinee, the advance direction is changed and the information on the position where the administered medicine is accumulated is lost, which causes a noise. Since the gamma ray loses energy by scattering, in the two-nuclide imaging of $^{99m}$Tc and $^{123}$I, for example, if a high-energy (159 keV) gamma ray emitted from the $^{123}$I is scattered in the examinee, the gamma ray may cause contamination of the image corresponding to a low-energy (140 keV) gamma ray emitted from the $^{99m}$Tc. For this contamination, conventionally is used the correction using the technique disclosed in The Journal of Nuclear Medicine, Vol. 34, No. 12, pp. 2216-2221, 1993 and JP-A-7-128450.

Figure 8:
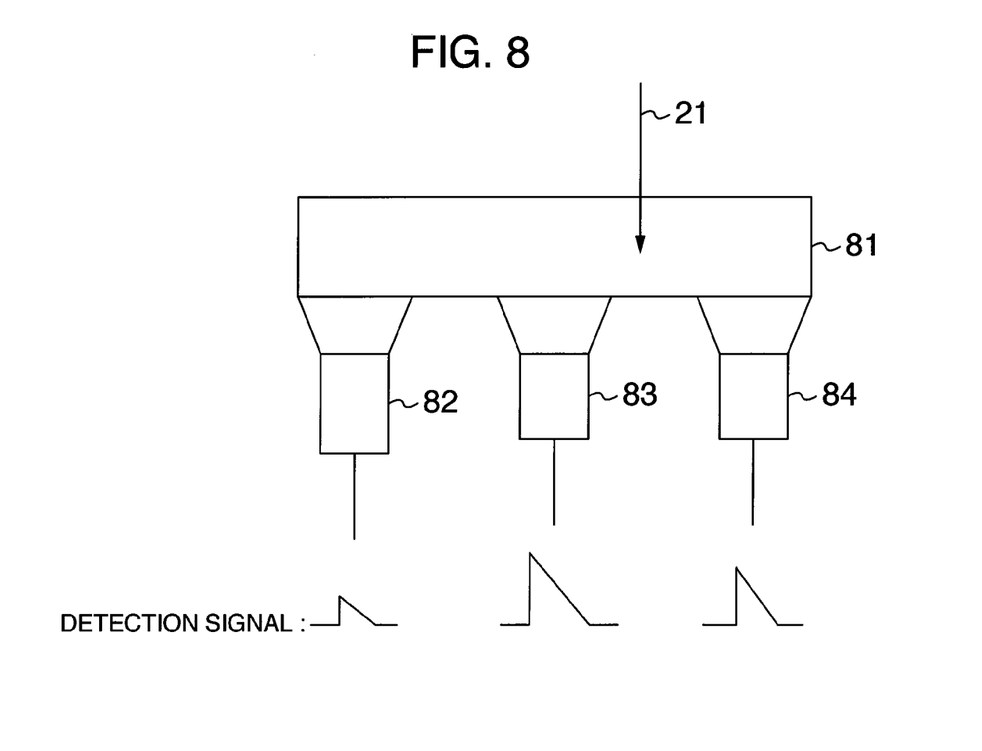
FIG. 8 shows an operation principle of an Anger type detector.
Figure 9:
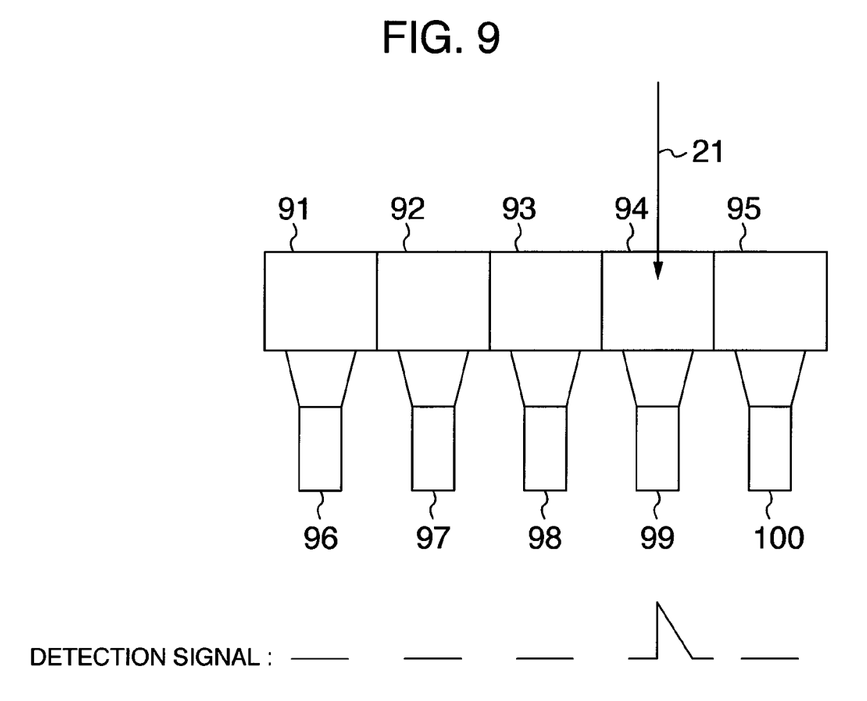
FIG. 9 shows an operation principle of a pixel type detector.

On the other hand, recently, study is made on a nuclear medical diagnosis apparatus of pixel type instead of the conventional Anger type. It should be noted that as is shown in FIG. 8, the Anger type detector includes a large-area flat crystal scintillator 81 (such as a monocrystal NaI (TI)) to which an optical device represented by a plenty of photoelectron amplification tubes 82, 83, 84 is attached. On the other hand, the pixel type detector, as shown in FIG. 9, includes small-size prismatic radiation detection devices such as NaI (TI) monocrystal pieces 91, 92, 93, 94, 95 and CdTe semiconductors which are arranged in a rectangular shape. In the case of the NaI(TI) monocrystal pieces, photoelectron amplification tubes 96, 97, 98, 99, 100 are mounted on each of them. In the Anger type detector, a plurality of optical devices (such as photoelectron amplification tubes 82, 83, 84) are mounted on one crystal scintillator 81 and the center of gravity of the light quantity is calculated so as to decide the detection position. However, an error is caused in the detection position by the calculation of the center of gravity. The pixel type is completely different from the Anger type. A signal is read out from each of the pixels (each NaI(TI) monocrystal pieces 91, 92, 93, 94, 95) and accordingly, the detection position decision is stable. Moreover, the pixel type detector using a semiconductor such as CdTe has an excellent energy resolution and attracts a great attention as the nuclear medical diagnosis apparatus of the next generation.

Figure 10:
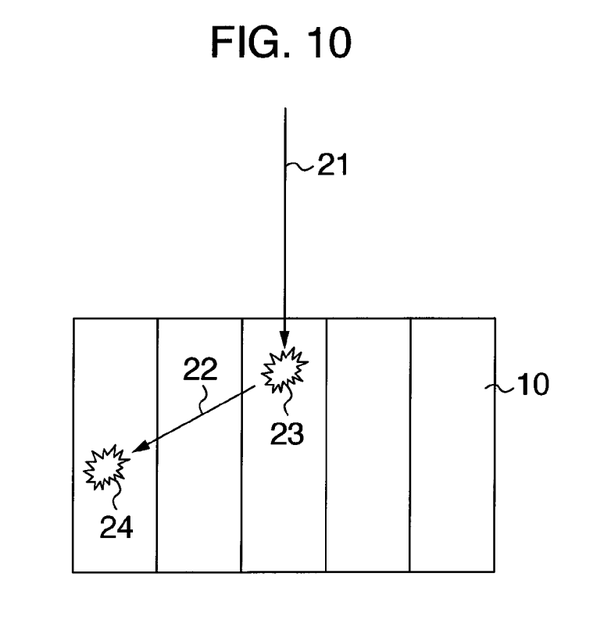
FIG. 10 shows an in-detector scattering in the pixel type detector.

The pixel type detector has a new contamination factor which is not remarkable in the Anger type detector. The factor is scattering of the gamma ray in the detector. As shown in FIG. 10, the gamma ray is not entirely absorbed by the detector 10 but may be scattered. When the scattered gamma ray causes total absorption in another pixel, the total energy is deposited to a plurality of pixels. For example, a gamma ray 21 of 159 keV emitted by $^{123}$I causes a scattering 23 in a predetermined pixel and deposits 19 keV while scattered gamma ray 22 of 140 keV is entirely absorbed by other pixel 24. In this case, it is considered that two independent energies of 140 keV and 19 keV are deposited. When the signal of 19 keV is lower than the lower level discrimination (LLD) of a circuit system and cannot be detected, only the signal of 140 keV remains. The output cannot be distinguished from the case when the gamma ray of 140 keV emitted by $^{99m}$Tc is totally absorbed, which causes contamination of the image corresponding to the gamma ray emitted by the $^{99m}$Tc.

Even if the radiation source distribution of the gamma ray emitted by the original $^{123}$I is point-like, energy is deposited to a pixel other than the target by scattering. This causes contamination of the image corresponding to the gamma ray emitted by the $^{99m}$Tc. When the administered medicine emits a gamma ray having energy higher than the set of the $^{123}$I and $^{99m}$Tc, the scattered gamma ray is easily transported farther.

Accordingly, contamination is generated in the further wider image region. The image corresponding to the gamma ray of the $^{99m}$Tc by the contamination, i.e., the image erroneously judged to be the image corresponding to the gamma ray emitted by the $^{99m}$Tc is generated in a pixel different from the radiation source distribution of the gamma ray of the $^{123}$I (even though correlation between them is present) and has no relationship with the radiation source distribution of the gamma ray of the $^{99m}$Tc. This problem cannot be solved by the conventional correction and causes degradation of the image.

SUMMARY OF THE INVENTION

It is therefore an object of the present invention to provide a nuclear medical diagnosis apparatus capable of obtaining a high-quality diagnosis image by preventing degradation of the image by the in-detector scattering when a multiple nuclide imaging is performed.

In order to achieve the aforementioned object, the present invention provides a nuclear medical diagnosis apparatus for performing a diagnosis by using gamma rays of a plurality of energies, the apparatus comprising: a detector for detecting the gamma rays; a signal processing unit for acquiring energy information and position information at respective detection points in the detector; an image creation unit for creating an image corresponding to the gamma ray of the high-energy side and an image corresponding to the gamma ray of the low-energy side according to energy information and position information at the respective detection points from the signal processing unit; an image correction operation unit which performs a convolution operation on the image corresponding to the gamma ray of the high-energy side created by the image creation unit so as to generate an image corresponding to the gamma ray of the high-energy size to be superimposed on the image corresponding to the gamma ray of the low-energy side; and a corrected image creation unit which subtracts the image corresponding to the gamma ray of the high-energy side and to be superimposed, from the image corresponding to the gamma ray of the low-energy side generated by the image creation unit, so that the subtraction prevents degradation of an image corresponding to the gamma ray of the low-energy side.

The present invention can prevent degradation of an image attributed to the in-detector scattering and accordingly, can provide a nuclear medical diagnosis apparatus capable of obtaining a preferable diagnosis image.

Other objects, features and advantages of the invention will become apparent from the following description of the embodiments of the invention taken in conjunction with the accompanying drawings.

DESCRIPTION OF THE INVENTION

Figure 1:
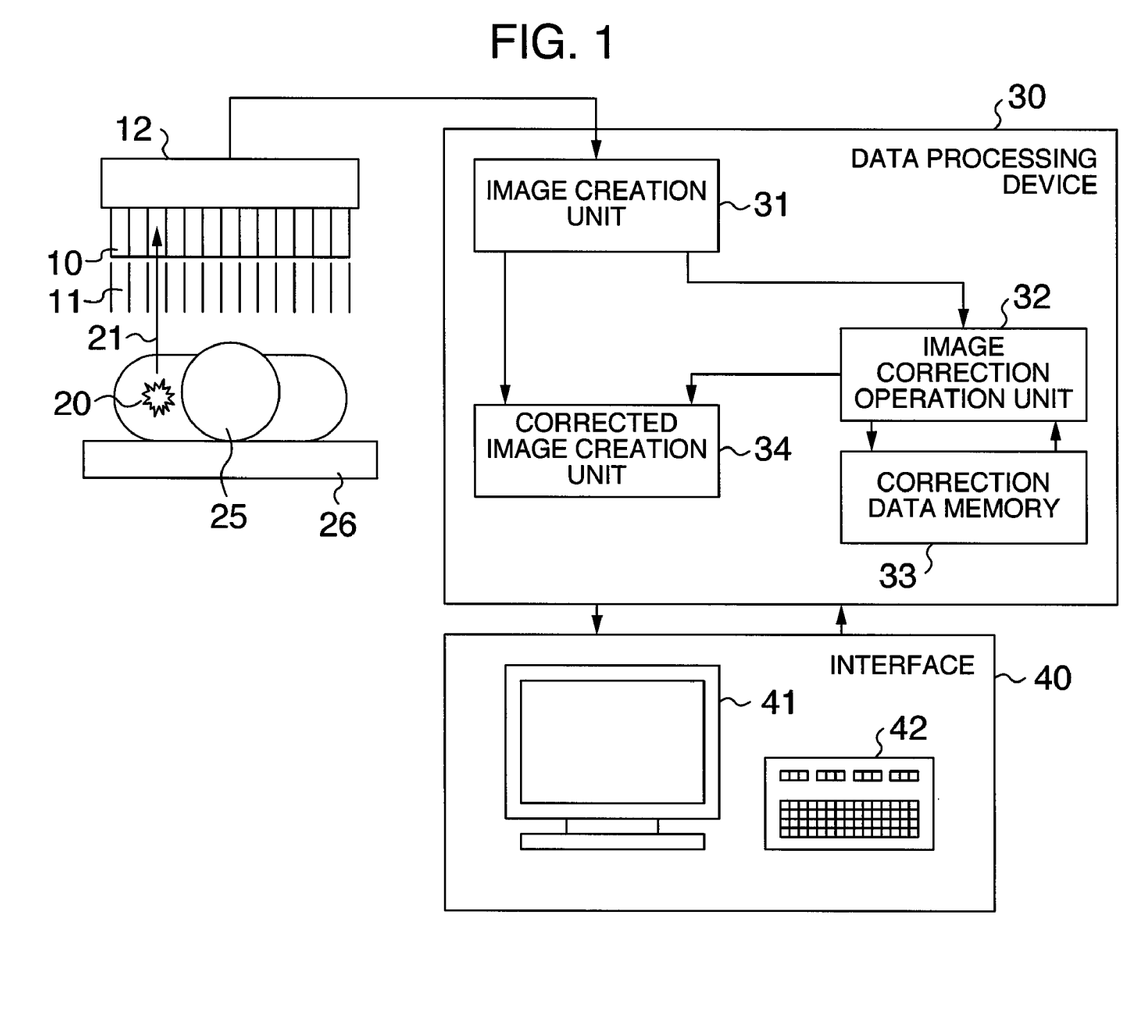
FIG. 1 is a block diagram showing a configuration of a nuclear medical diagnosis device according to a first embodiment of the present invention.
Figure 2A:
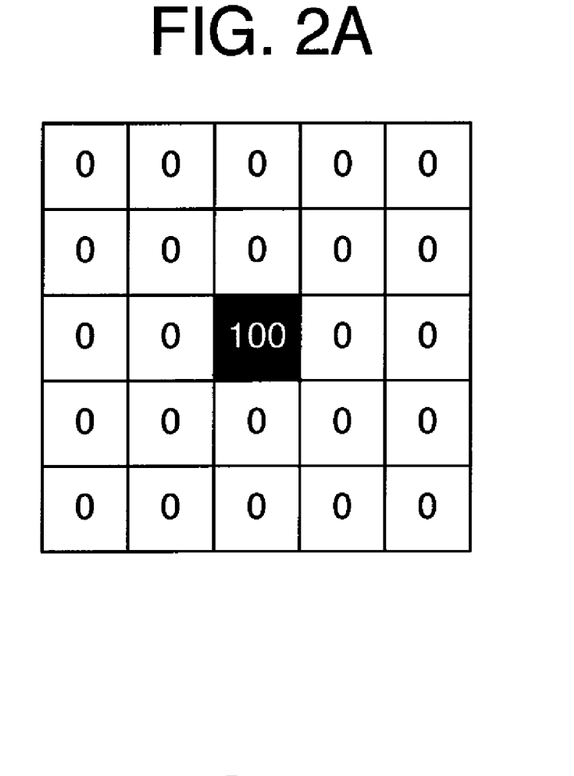
FIG. 2A shows a contamination state when the gamma ray of 159 keV emitted from the $^{123}$I comes into one pixel.
Figure 2B:
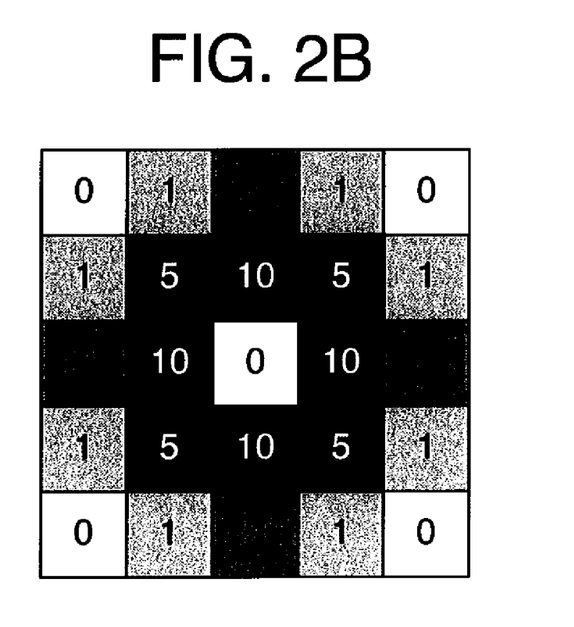
FIG. 2B shows a contamination state when the gamma ray of 159 keV emitted from the $^{123}$I comes into one pixel.
Figure 3:
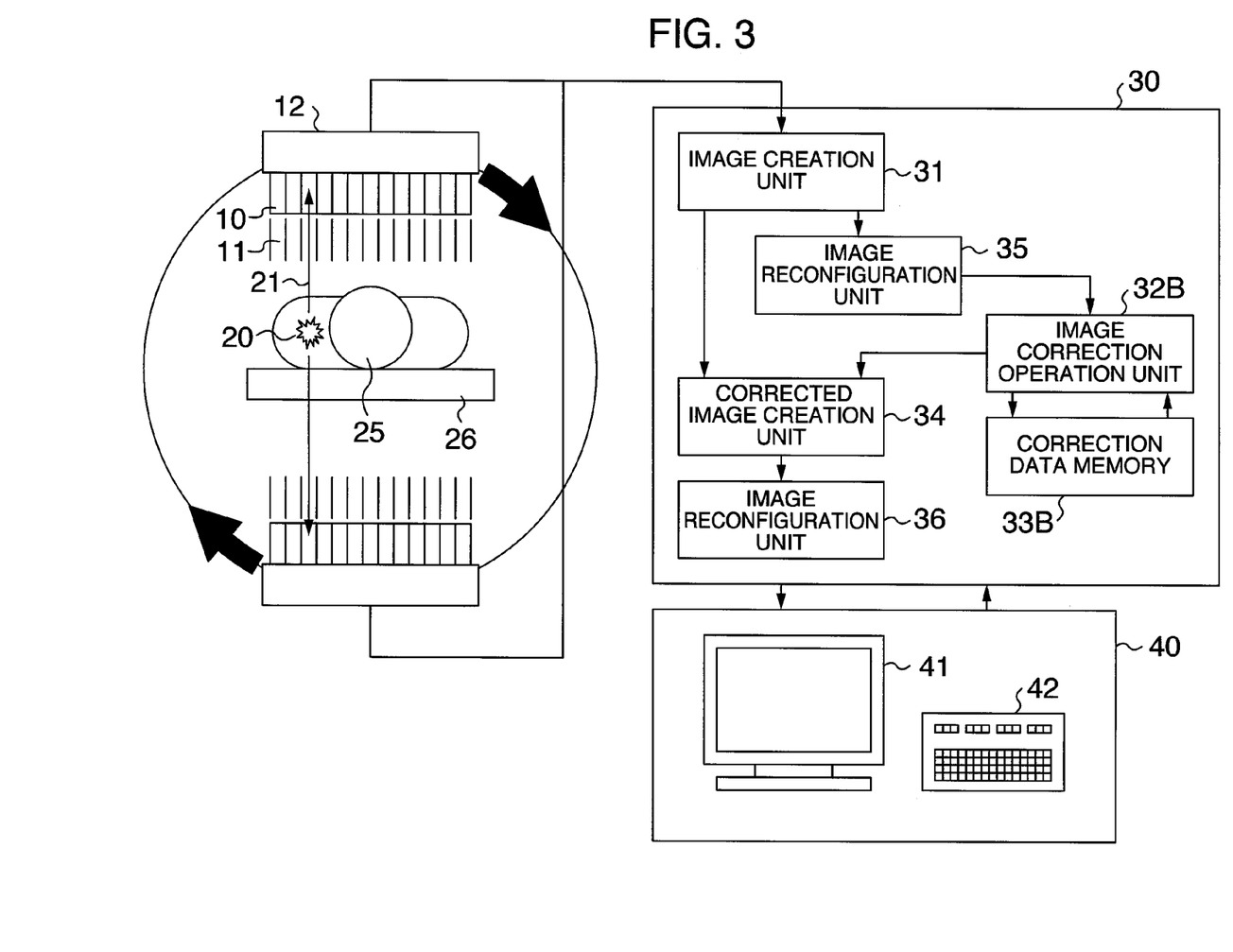
FIG. 3 is a block diagram showing a configuration of the nuclear medical diagnosis apparatus according to a second embodiment of the present invention.
Figure 4:
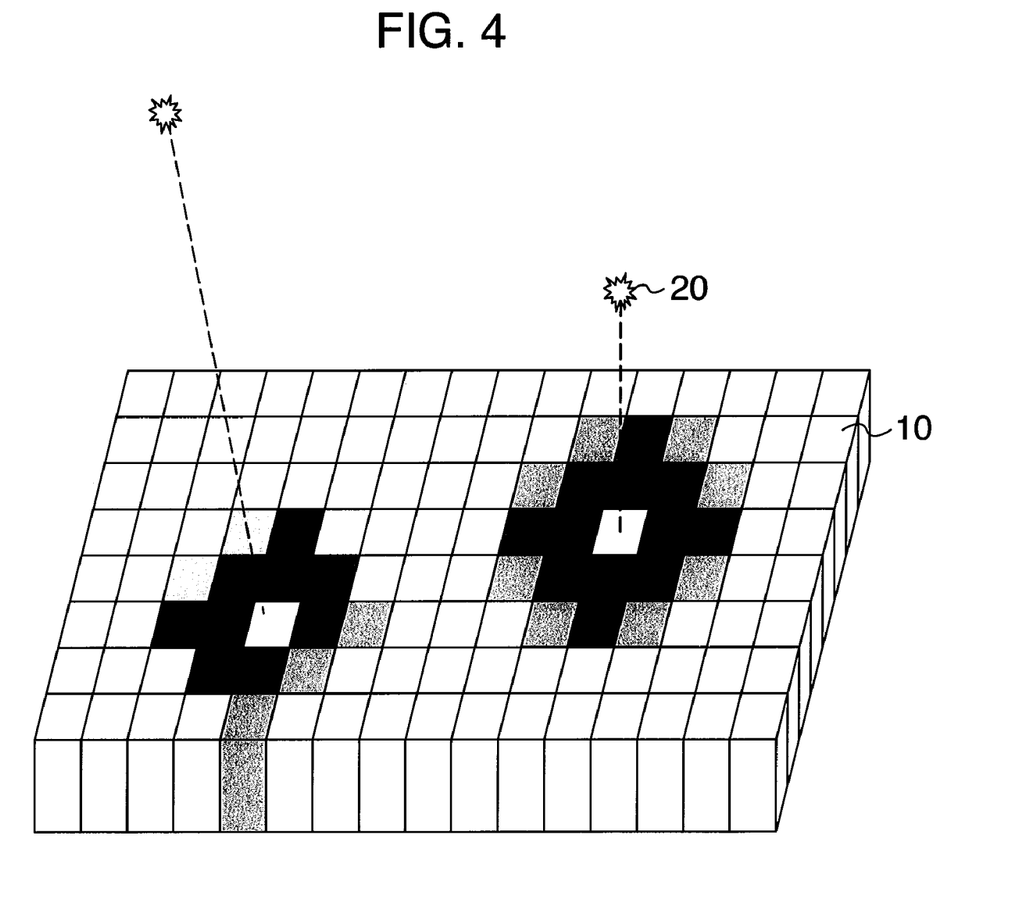
FIG. 4 schematically shows a difference between contamination images generated by the positional relationship between the radiation source of the gamma ray of 159 keV emitted from the $^{123}$I and the detector.
Figure 5:
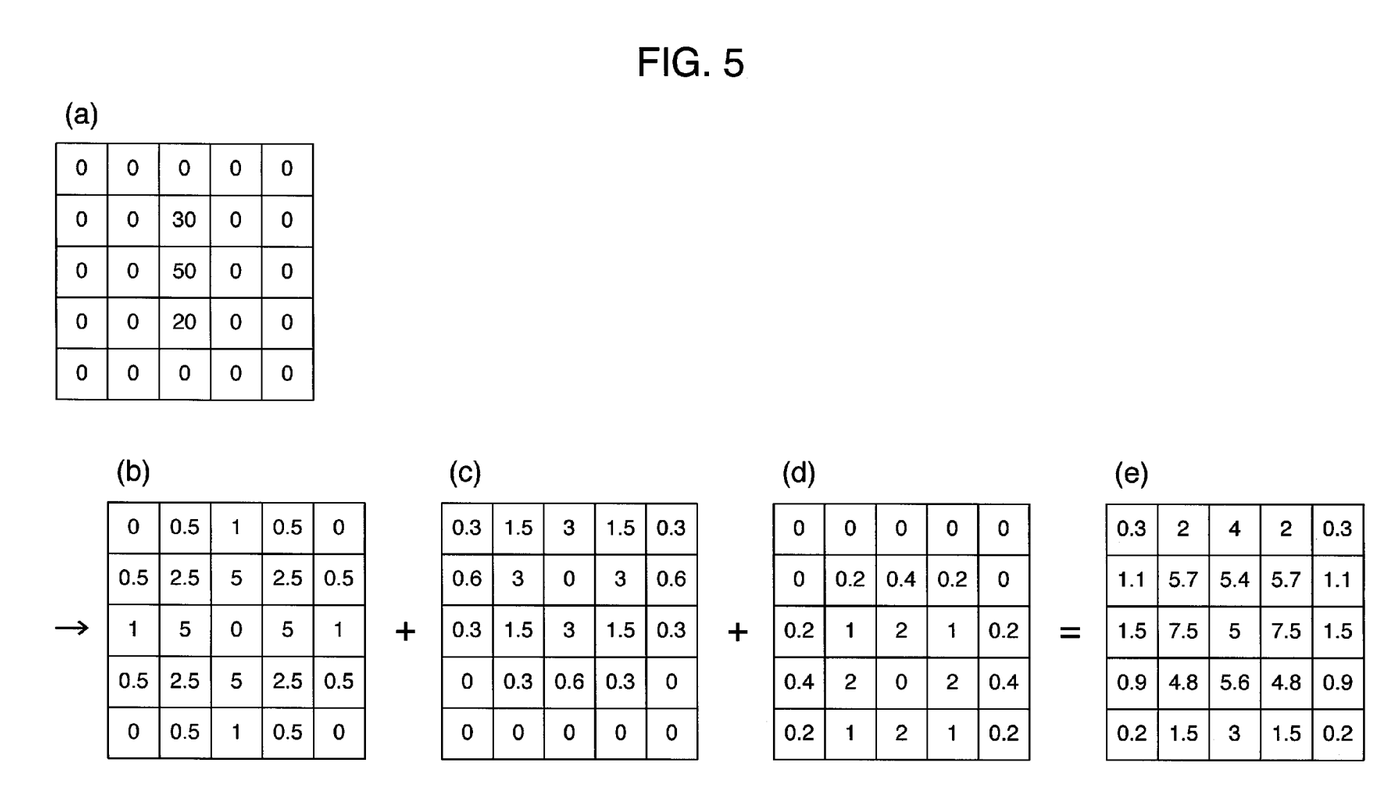
FIG. 5 shows a method how to perform convolution operation.

Description will now be directed to embodiments of the present invention with reference to FIG. 1 to FIG. 6. FIG. 1 is a block diagram showing a configuration of a nuclear medical diagnosis apparatus as a first embodiment of the present invention. FIGS. 2A and 2B shows the states of contamination when a gamma ray of 159 keV emitted by $^{123}$I comes into one pixel. FIG. 3 is a block diagram showing a configuration of a nuclear medical diagnosis apparatus (SPECT device) as the second embodiment of the present invention. FIG. 4 schematically shows a difference between contamination images generated by the positional relationship between the radiation source of the gamma ray of 159 keV emitted from the $^{123}$I and the detector. FIG. 5 shows a method how to perform convolution operation. FIGS. 6A, 6B, 6C show an example of contamination image data (correction data) stored in a correction data memory.

EMBODIMENT 1

Explanation will be given on the nuclear medical diagnosis apparatus according to the first embodiment. A medicine administered to an examinee 25 supported at 26 is accumulated in tumor or the like. A gamma ray 21 is emitted from the accumulation portion of the administered medicine such as the tumor. The emitted gamma ray 21 is detected by a detector 10 constituting a gamma camera. Here, the detector 10 may be crystal scintillator such as NaI(Tl), GSO(Ce), LSO(Ce), BGO to which an optical device 11 (a photoelectron amplification tube, a photo diode, an avalanche photo diode, etc.) is attached or a semiconductor (silicone, germanium, CdTe, CZT, TlBr, HgI$_2$, etc.). The gamma ray detected by the detector 10 is converted into an electric signal and sent to an amplification/ADC (analog-to-digital converter) circuit 12 of the latter stage. It should be noted that the detector 10 is a pixel type detector.

In the amplification/ADC circuit 12, the signal of the gamma ray is converted into digital pulse height value information typically via a pre-amplification unit, a waveform shaping unit, a peak hold unit, and an ADC. The pulse height value information and the position information on the detector which has detected the gamma ray are sent to an image creation unit 31 in a data processing device 30 of the latter stage. The position information on the detector can be judged by identifying the amplification/ADC circuit 12 from which the pulse height information has been sent when each pixel has an amplification/ADC circuit 12. It should be noted that the pulse height value information and the detector position can be generated from a detection signal outputted from the detector 10 by using the method disclosed in paragraphs 0034 to 0037 of JP-A-2005-17142.

The image creation unit 31 judges whether the detected gamma ray energy is contained in an energy window specified by the user according to the pulse height value information sent from the amplification/ADC circuit 12. If yes, this is considered to be a valid event and the count of the corresponding position in the image is incremented by one according to the position information. Since a plurality of energy windows can be specified via the input device 42 (see "INTERFACE 40" in FIG. 1), it is possible to obtain uncorrected images corresponding to the gamma rays of different energies. For example, when performing two-nuclide imaging using $^{99m}$Tc and $^{123}$I, it is possible to set the energy window of $^{99m}$Tc via the input device and the energy window of $^{123}$I so as to obtain an uncorrected image corresponding to the gamma ray of 140 keV emitted from the $^{99m}$Tc and the gamma ray of 159 keV emitted from the $^{123}$I It should be noted that the energy window 72 and the energy window 73 in FIG. 7 are the energy window of the $^{99m}$Tc and the energy window of the $^{123}$I set via the input device 42, respectively.

The image obtained by the image creation unit 31 has a contamination component caused by scattering of the gamma ray in the detector. Hereinafter, explanation will be given on the operation of the data processing device 30 as an example of two-nuclide imaging using $^{99m}$Tc and $^{123}$I. An image corresponding to the gamma ray of 159 keV emitted from the high-energy 123, is subjected to convolution operation in the image correction operation unit 32 (the convolution operation will be detailed later). That is, the gamma ray of 159 keV emitted by the $^{123}$I causes an in-detector scattering so that a contamination image (image for correction) to be superimposed on the image corresponding to the gamma ray of 140 keV emitted by the $^{99m}$Tc is obtained by the convolution operation.

The contamination image obtained in the image correction operation unit 32 is sent to a corrected image creation unit 34 where it is subtracted from an uncorrected image corresponding to the gamma ray of 140 keV emitted by the $^{99m}$Tc generated in the image creation unit 31. As a result, it is possible to obtain a preferable image (image corresponding to the gamma ray of 140 keV emitted from the $^{99m}$Tc) from which contamination due to in-detector scattering has been removed. The obtained image is supplied via a display device 41 (see "INTERFACE 40" in FIG. 1) for nuclear medical diagnosis.

It should be noted that when simultaneous imaging by using gamma rays of three or more energies is performed, firstly, a contamination of the gamma ray of the highest energy, in the image corresponding to the gamma ray of the second highest energy, is corrected. Next, according to the image of the gamma ray of the highest energy and the corrected image corresponding to the gamma ray of the second highest energy, contaminations of the gamma rays of the highest energy and the second highest energy, in the image corresponding to the gamma ray of third highest energy, are corrected. Hereinafter, correction is successively performed in the descending order of the energies of the gamma rays, so as to obtain an image in which the in-detector scattering is corrected for the gamma rays of all the energies.

A detailed explanation will be given on the convolution operation in the image correction operation unit 32. In order to perform the calculation, for example, as shown in FIG. 2A, when the gamma ray of 159 keV emitted by the $^{123}$I comes only into one pixel of the 5-row/5-column pixel type detector and 100 counts are detected, as shown in FIG. 2B, it is sufficient to know the distribution of the peripheral count values at an energy window 72 of the $^{99m}$Tc side. The reason of this will be detailed later. In FIG. 2A and FIG. 2B, the gamma ray of 159 keV emitted by the $^{123}$I comes into only the one pixel at the center and only the peripheral count value distribution at the energy window 72 of the $^{99m}$Tc side is shown when 100 counts are detected. However, it is also necessary to show the peripheral count value distribution at the energy window 72 of the $^{99m}$Tc side when the gamma ray of 159 keV emitted by the $^{123}$I comes into other one pixel than one pixel at the center. That is, in the case of 5-row/5-column pixel type detector, there are 25 pixels into which the gamma ray of 159 keV emitted by the $^{123}$I comes. When the gamma ray of 159 keV emitted by the $^{123}$I comes into each of the pixels, it is necessary to show the peripheral count value distribution at the energy window 72 of the $^{99m}$Tc side. For this, a correction data memory 33 contains data on 25 cases of the peripheral count value distributions at the energy window 72 of the $^{99m}$Tc side when the gamma ray of 159 keV emitted by the $^{123}$I comes into each of the pixels when using a 5-row/5-column pixel type detector and a 100 count value is detected.

When performing the convolution operation, as has been described above, for example, when the gamma ray of 159 keV emitted by the $^{123}$I comes into only one pixel of the 5-row/5-column pixel type detector, it is sufficient to know the peripheral count value distribution at the energy window 72 of the $^{99m}$Tc side. The reason is as follows. For example, there is a case that the gamma ray of 159 keV emitted by the $^{123}$I may come into a plurality of pixels. In this case, by using the processes (1) to (5) explained below, it is possible to obtain the peripheral count value distribution at the energy window 72 of the $^{99m}$Tc side when the gamma ray of 159 keV emitted by the $^{123}$I is incident.

(1) Firstly, one of pixels into which the gamma ray has come is selected and a calculation is performed to obtain a peripheral count value distribution in the energy window 72 of the $^{99m}$Tc side when it is assumed that a predetermined dose of the gamma ray of 159 keV emitted by the $^{123}$I has come only into the selected pixel. When obtaining this peripheral count value distribution, data recorded in the correction data memory 33 is used.

(2) Next, one of the pixels into which the gamma ray has come other than the pixel selected in the aforementioned (1) is selected and a calculation is performed to obtain a peripheral count value distribution in the energy window 72 of the $^{99m}$Tc side when it is assumed that a predetermined dose of the gamma ray of 159 keV emitted by the $^{123}$I has come only into the selected pixel. When acquiring this peripheral count value distribution, data recorded in the correction data memory 33 is used.

(3) If there is one or more pixels not selected among the pixels into which the gamma ray has come, one of such pixels is selected and a calculation is performed to obtain a peripheral count value distribution in the energy window 72 of the $^{99m}$Tc side when it is assumed that a predetermined dose of the gamma ray of 159 keV emitted by the $^{123}$I has come only into the selected pixel. When acquiring this peripheral count value distribution, data recorded in the correction data memory 33 is used.

(4) The aforementioned operation (3) is repeated until all the pixels into which the gamma ray has come are selected and a calculation is performed to obtain a peripheral count value distribution in the energy window 72 of the $^{99m}$Tc side when it is assumed that a predetermined dose of the gamma ray of 159 keV emitted by the $^{123}$I has come into each of the selected pixel.

(5) A calculation is performed to obtain a sum of peripheral count value distributions in the energy window 72 of the $^{99m}$Tc side when it is assumed that a predetermined dose of the gamma ray of 159 keV emitted by the $^{123}$I has come only into each of the pixels. That is, the sum of the peripheral count value obtained by the aforementioned (1) to (4) is obtained. This sum of the peripheral count values is the peripheral count value distributions in the energy window 72 of the $^{99m}$Tc side when the gamma ray of 159 keV emitted by the $^{123}$I to the plurality of pixels.

Referring to FIG. 5, a more specific explanation will be given on the operation performed to obtain a peripheral count value distribution in the energy window 72 of the $^{99m}$Tc side when the gamma ray of 159 keV emitted by the $^{123}$I has come into a plurality of pixels. For example, the (a) of FIG. 5 shows a case when the gamma ray of 159 keV emitted from the $^{123}$I has come into three pixels. In this case, by using the data recorded in the correction data memory 33, as shown in the (b) of FIG. 5, the peripheral count value distributions in the energy window 72 of the $^{99m}$Tc side when it is assumed that only 50 counts of the gamma ray of 159 keV emitted by the $^{123}$I is detected in the portion indicated in (1) described below, are calculated. It should be noted that the method for obtaining the peripheral count value distribution shown in the (b) of FIG. 5 will be detailed later. Similarly, the (c) of FIG. 5 shows a peripheral count value distributions in the energy window 72 of the $^{99m}$Tc side when it is assumed that only 30 counts in the gamma ray of 159 keV emitted from the $^{123}$I are detected in the portion indicated by (2) described below. The (d) of FIG. 5 shows a peripheral count value distributions in the energy window 72 of the $^{99m}$Tc side when only 20 counts in the gamma ray of 159 keV emitted by the $^{123}$I are detected in the portion indicated by (3) described below. The method for obtaining the peripheral count value distribution shown in the (c) and (d) of FIG. 5 will be detailed later.

(1) Pixel at the center
(2) Pixel adjacent to the central pixel and immediately above the central pixel
(3) Pixel adjacent to the central pixel and immediately below the central pixel Then, calculations are performed to obtain a sum of the peripheral count value distributions in the energy window 72 of the $^{99m}$Tc side: when it is assumed that only the 50 counts in the gamma ray of 159 keV emitted by the $^{123}$I are detected at the portion indicated by (1); when it is assumed that only the 30 counts in the gamma ray of 159 keV emitted by the $^{123}$I are detected at the portion indicated by (2); and when it is assumed that only the 20 counts in the gamma ray of 159 keV emitted by the $^{123}$I are detected at the portion indicated by (3). This sum is the peripheral count value distribution in the energy window 72 of the $^{99m}$Tc side when the gamma ray of 159 keV emitted to three pixels by the $^{123}$I. That is, the peripheral count distribution shown in the (e) of FIG. 5 is the peripheral count value distribution in the energy window 72 of the $^{99m}$Tc side when the gamma ray of 159 keV emitted by the $^{123}$I comes into the three pixels. As has been described above, it is possible to obtain the peripheral count value distribution in the energy window 72 of the $^{99m}$Tc side when the gamma ray of 159 keV emitted by the $^{123}$I comes into the three pixels.

In the nuclear medical diagnosis apparatus according to the present embodiment, explanation has been given on the specific operation for a case to obtain the peripheral count value distribution in the energy window 72 of the $^{99m}$Tc side when the gamma ray of 159 keV emitted by the $^{123}$I comes into the three pixels. Even in a case other than the case when the gamma ray of 159 keV emitted by the $^{123}$I comes into the three pixels such as a case when the gamma ray of 159 keV emitted by the $^{123}$I comes into two pixels or a case when the gamma ray of 159 keV emitted by the $^{123}$I comes into four or more pixels, it is possible to similarly obtain the peripheral count value distribution in the energy window 72 of the $^{99m}$Tc side. The image generated by the peripheral count value distribution becomes the contamination image. It should be noted that the nuclear medical diagnosis apparatus according to the present embodiment has been explained in the case using 5-row/5-column pixel type detector. However, the contamination image can also be generated in the same way when using a detector other than the 5-row-/5-column pixel type detector.

Hereinafter, explanation will be given on the method how to obtain the peripheral count value distributions shown in (b), (c), (d) of FIG. 5. It should be noted that as has been described above, the correction data memory 33 contains data on 25 ways of the peripheral count value distribution in the energy window 72 of the $^{99m}$Tc side when the 5-row/5-column pixel type detector is used, the gamma ray of 159 keV emitted by $^{123}$I comes into the respective pixels, and 100 counts are detected. In order to obtain data on the peripheral count value distributions shown in (b), (c), (d) of FIG. 5, among the 25 ways of data, it is necessary to use data indicating the peripheral count value distributions in the energy window 72 of the $^{99m}$Tc side when the gamma ray of 159 keV emitted by the $^{123}$I comes into the respective portions of the aforementioned (1) to (3).

In the (a) of FIG. 5, 50 counts of the gamma ray of 159 keV emitted by the $^{123}$I are detected in a pixel of the aforementioned portion (1). When the 50 counts of the gamma ray are detected, each pixel value of the peripheral count value distribution in the energy window 72 of the $^{99m}$Tc side is half of each corresponding pixel value in the peripheral count value distribution in the energy window 72 of the $^{99m}$Tc side when it is assumed that the gamma ray of 159 keV emitted by the $^{123}$I comes only into the pixel of the aforementioned portion (1) and 100 counts are detected.

Similarly, in the (a) of FIG. 5, 30 counts of the gamma ray of 159 keV emitted by the $^{123}$I are detected in a pixel of the aforementioned portion (2). When the 30 counts of the gamma ray are detected, each pixel value of the peripheral count value distribution in the energy window 72 of the $^{99m}$Tc side is 30% of each corresponding pixel value in the peripheral count value distribution in the energy window 72 of the $^{99m}$Tc side when it is assumed that the gamma ray of 159 keV emitted by the $^{123}$I comes only into the pixel of the aforementioned portion (2) and 100 counts are detected.

Furthermore, in the (a) of FIG. 5, 20 counts of the gamma ray of 159 keV emitted by the $^{123}$I are detected in a pixel of the aforementioned portion (3). When the 20 counts of the gamma ray are detected, each pixel value of the peripheral count value distribution in the energy window 72 of the $^{99m}$Tc side is 20% of each corresponding pixel value in the peripheral count value distribution in the energy window 72 of the $^{99m}$Tc side when it is assumed that the gamma ray of 159 keV emitted by the $^{123}$I comes only into the pixel of the aforementioned portion (3) and 100 counts are detected.

Figure 6A:
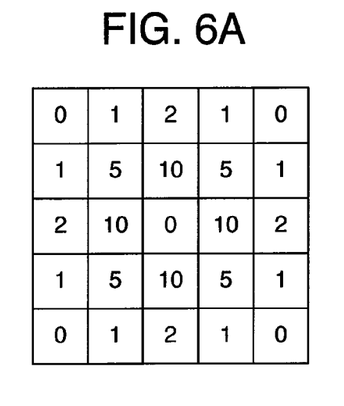
FIG. 6A shows an example of contamination image data (correction data) stored in a correction data memory.
Figure 6B:
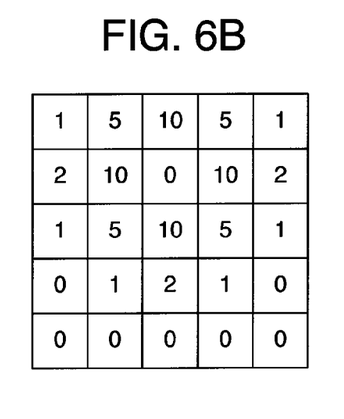
FIG. 6B shows an example of contamination image data (correction data) stored in a correction data memory.
Figure 6C:
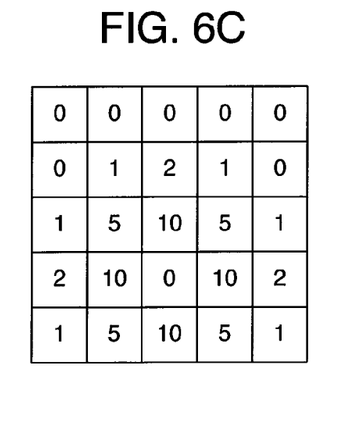
FIG. 6C shows an example of contamination image data (correction data) stored in a correction data memory.

FIG. 6A, FIG. 6B, and FIG. 6C show the data indicating the peripheral count value distribution in the energy window 72 of the $^{99m}$Tc side when it is assumed that the gamma ray emitted by the $^{123}$I comes into only the pixels of the aforementioned portion (1), only the pixels of the aforementioned portion (2), and only the pixels of the aforementioned portion (3), respectively. As has been described above, since 50 counts of the gamma ray of 159 keV emitted by the $^{123}$I are detected by the pixels of the aforementioned portion (1), the peripheral count value distribution in the energy window 72 of the $^{99m}$Tc side when the 50 counts of the gamma ray are detected corresponds to the (b) of FIG. 5 according to FIG. 6A.

Similarly, since 30 counts of the gamma ray of 159 keV emitted by the $^{123}$I are detected by the pixels of the aforementioned portion (2), the peripheral count value distribution in the energy window 72 of the $^{99m}$Tc side when the 30 counts of the gamma ray are detected corresponds to the (c) of FIG. 5 according to FIG. 6B. Furthermore, since 20 counts of the gamma ray of 159 keV emitted by the $^{123}$I are detected by the pixels of the aforementioned portion (3), the peripheral count value distribution in the energy window 72 of the $^{99m}$Tc side when the 20 counts of the gamma ray are detected corresponds to the (d) of FIG. 5 according to FIG. 6C.

Next, explanation will be given on the method how to obtain data (data recorded in the correction data memory 33) on the 25 ways indicating the respective peripheral count value distributions in the energy window 72 of the $^{99m}$Tc side when the gamma ray of 159 keV emitted by the $^{123}$I comes into the respective pixels by using the 5-row/5-column pixel type detector. When obtaining the 25 ways of data, the gamma ray in-detector scattering is a probability process (a probability phenomenon which transits as the time elapses) and accordingly, for example, the Monte Carlo simulation of the radiation transport is performed. It should be noted that the Monte Carlo simulation of the radiation transport is a simulation handling the three-dimensional behavior of a radiation in a material.

Instead of performing the Monte Carlo simulation of the radiation transport, it is also possible to actually perform an experiment of applying the gamma ray only to one pixel. By using the actually measured data and the 5-row/5-column pixel type detector, it is possible to obtain data on the 25 ways indicating the respective peripheral count value distributions in the energy window 72 of the $^{99m}$Tc side when the gamma ray of 159 keV emitted by the $^{123}$I comes into the respective pixels.

EMBODIMENT 2

Description will now be directed to a nuclear medical diagnosis apparatus (SPECT apparatus) according to a second embodiment. Like the nuclear medical diagnosis apparatus according to the first embodiment, a medicine administered to an examinee 25 is accumulated in a tumor or the like. The gamma ray 21 emitted from the accumulation portion of the administered medicine is detected by a detector 10 and converted into an electric signal, which is subjected to the same processes as in the nuclear medical diagnosis apparatus of the first embodiment by using the amplification/ADC control circuit 12 and the image creation unit 31 so as to obtain an uncorrected image corresponding to the respective gamma rays of different energies. For example, when performing two-nuclide imaging using $^{99m}$Tc and $^{123}$I, it is possible to obtain an uncorrected image corresponding to the gamma ray of 140 keV emitted from the $^{99m}$Tc and an image corresponding to the gamma ray of 159 keV emitted from the $^{123}$I by setting an energy window 72 of the $^{99m}$Tc side and an energy window 73 of the $^{123}$I side via the input device 42. In the nuclear medical diagnosis apparatus (SPECT apparatus) according to the present embodiment, by performing measurement while changing the position of the detector 10, it is possible to create a plenty of uncorrected images corresponding to the gamma ray of 140 keV emitted by the $^{99m}$Tc and a plenty of images corresponding to the gamma ray of 159 keV emitted by the $^{123}$I.

According to a plenty of images corresponding to the gamma ray of 159 keV emitted by a plenty of the $^{123}$I created in the image creation unit 31, an image reconfiguration unit 35 configures three-dimensional distribution of the 159-keV gamma radiation source (tumor or other accumulation portion of the administered medicine) and outputs it to an image correction operation unit 32B. According to the three-dimensional distribution of the radiation source (tumor or other accumulation portion of the administered medicine) of the 159 keV gamma ray emitted by the $^{123}$I and the contamination image data recorded in the correction data memory 33B, the image correction operation unit 32B obtains respective contamination images coming into images corresponding to the gamma ray of 140 keV emitted by the $^{99m}$Tc when the detector 10 are positioned at respective positions. That is, a contamination image generated when the gamma ray of 159 keV emitted by the $^{123}$I is obtained. It should be noted that the contamination image data are data on a contamination image which comes into an image corresponding to the 140-keV gamma ray emitted by the $^{99m}$Tc when the 159-keV gamma ray emitted by the $^{123}$I is applied.

In the corrected image creation unit 34, the aforementioned respective contamination images are subtracted from the respective corresponding images (uncorrected images corresponding to the 140-keV gamma ray emitted by the $^{99m}$Tc) outputted from the corresponding image creation unit 31 so as to obtain a preferable image (an image corresponding to the 140-keV gamma ray emitted by the $^{99m}$Tc) from which contamination caused by the in-detector scattering is removed. The image is reconfigured into a three-dimensional distribution image of the radiation source (tumor or other accumulation portion of the medicine) of the 140 keV gamma ray emitted by the $^{99m}$Tc in an image reconfiguration unit 36, which is used for nuclear medical diagnosis via the display device 41.

Explanation will be given on the operation performed to obtain the contamination image in the image correction operation unit 32B. In order to perform the operation, it is enough to know how the counting is performed in the energy window 72 of the $^{99m}$Tc side when the radiation source of the 159-keV gamma ray emitted by the $^{123}$I is at respective positions with respect to the detector 10 (for example, directly above the detector 10 or obliquely above the detector 10) and at respective distances from the detector 10 as shown in FIG. 4. The way of counting may also be obtained by performing the Monte Carlo simulation of the radiation transport in the image correction operation unit 32B according to the three-dimensional distribution of the radiation source (tumor or other accumulation portion of the administered medicine) of 159 keV gamma ray emitted by the $^{123}$I which has been obtained in the image reconfiguration unit 35. It should be noted that the Monte Carlo simulation of the radiation transport is a simulation handling the three-dimensional behavior of the radiation in a material.

In addition to the Monte Carlo simulation of the radiation transport, it is possible to accumulate in advance in the correction data memory 33B, contamination images when the radiation source 20 of the gamma ray of 159 keV emitted by the $^{123}$I is located, for example, directly above a detector 10 and directly above an adjacent detector 10 and the interpolation operation and the convolution are performed as is described in the nuclear medical diagnosis apparatus of the first embodiment so as to perform operation to obtain a contamination image. It should be noted that the interpolation operation is an operation for obtaining data when data are not continuous but discrete. For example, in order to obtain a contamination image when the radiation source 20 of the gamma ray of 159 keV emitted by the $^{123}$I is located at the end portion of the detector 10, the contamination image obtained when the radiation source 20 is directly above the detector and the contamination image obtained when the radiation source 20 is directly above the adjacent detector are averaged and the average is assumed to be the contamination image when the radiation source 20 is located at the end portion of the detector 10.

In the same way as the nuclear medical diagnosis apparatus of the aforementioned first embodiment, the data at a representative point to be recorded in the correction data memory 33B may be based on the Monte Carlo simulation or may be actually measured.

SUMMARY

In the nuclear medical diagnosis apparatus of the first and the second embodiment, the contamination may be reduced by narrowing the energy window when creating an image corresponding to each of the gamma rays (such as the gamma ray of 159 keV emitted by the $^{123}$I and the gamma ray of 140 keV emitted by the $^{99m}$Tc) in the image creation unit 31. Accordingly, the contamination image created by the image correction operation unit 32, 32B depends on the energy window. Consequently, by accumulating data on representative energy windows as a database in the correction data memory 33, 33B so as to create a contamination image by the interpolation, it is possible to reduce the time required for the correction.

The correction of the in-detector scattering according to the present invention is to be applied to a completely different object from the conventional one such as an in-examinee scattering or a leak-in caused by an insufficient energy resolution. For this, it is possible to add the conventional correction independently to the correction of the present invention so as to prevent not only the image degradation due to the in-detector scattering but also the image degradation caused by an in-examinee scattering and a leak-in caused by an insufficient energy resolution.

Moreover, for the nuclear medical diagnosis apparatus according to the first and the second embodiment, explanation has been given on an example using the pixel type detector in which the detector is 1-pixel/1-detection element, i.e., a detector in which a photoelectron amplification tube is mounted on each of the plenty of small-size prism-shaped NaI(TI) mono-crystals which are arranged in a square or the detector in which a read line is attached to each of a plenty of CdTe crystals arranged in a square. However, the detector may not be 1-pixel/1-detection element type. For example, like a strip-type detector (such as the detector disclosed in FIG. 10 of JP-A-2005-109269), it is possible to use a plurality of X-axis strip electrodes and Y-axis strip electrodes which extend orthogonally intersecting one another so as to obtain the radiation incident position as the X-axis detection position and the Y-axis detection position, after which coincident measurement is performed to obtain the two-dimensional incident position information, thereby preventing image degradation attributed to the in-detector scattering in the same way.

As a case different from the in-detector scattering, when the pixel size is small, upon detection of a primary electron, i.e., a gamma ray by a detector, it is impossible to ignore the range (distance of movement from the moment when the primary electron or a characteristic X-ray starts moving until the moment when they stop) of an electron which has received energy from the gamma ray and the characteristic X-ray, i.e., a positive hole generated by a jump out of an electron which is embedded by other electron and the X-ray flying transmitted by the energy accumulated in the positive hole. As a result, the primary electron and the characteristic X-ray may move to another pixel (escape). By this movement, for example, the primary electron or the characteristic X-ray receives the energy of 140 keV from the gamma ray of 159 keV and if the primary electron or the characteristic X-ray gives the 140 keV energy to another pixel, the 159 keV event may be changed to 140 keV, which in turn may cause contamination. Such an escape process (movement of a primary electron or characteristic X-ray to another pixel) also causes image degradation like the in-detector scattering. This image degradation can also be prevented by the present invention.

Furthermore, when one detection element is formed by a plurality of pixels and an event occurs at a boundary between pixels, a signal carrier (ultraviolet light or visible light in the case of the crystal scintillator or electron positive hole pair in the case of semiconductor) generated in the detector by energy deposit may be divided to pixels of the both sides and read out. This may cause the similar contamination generated by the aforementioned escape process (movement of a primary electron or characteristic X-ray to another pixel). In addition to this, when one gamma ray is detected by a plurality of pixels, the process of read out of the signal from the plurality of pixels may cause the similar contamination. The present invention can prevent the image degradation caused by the contamination generated in these processes.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A nuclear medical diagnosis apparatus for performing a diagnosis by using gamma radiation of a plurality of energies, the apparatus comprising:
   a detector for detecting radiation;
   a signal processing unit for acquiring information on an energy and a position from a signal of the detector;
   an image creation unit for creating an image based on an energy corresponding to the gamma radiation of each of energies according to the data from the signal processing unit;
   an image correction operation unit which performs a convolution operation on the image corresponding to the gamma radiation of the higher-energy side among images created for the respective energies by the image creation unit, wherein the convolution operation is executed by applying count values to be subtracted from a lower-energy side image to peripheral pixels of a pixel for which higher-energy gamma radiation is detected; and
   a corrected image creation unit for subtracting the correction image from an image corresponding to the gamma radiation of the lower-energy side among the images created for respective energies by the image creation unit.

2. The nuclear medical diagnosis apparatus as claimed in claim 1, wherein
   the detector is formed by a plurality of detection elements.

3. The nuclear medical diagnosis apparatus as claimed in claim 2, wherein the detector has a plurality of pixels, each of which is formed by one detection element.

4. The nuclear medical diagnosis apparatus as claimed in claim 1, wherein
the detector is formed by a semiconductor radiation detector.

5. A nuclear medical diagnosis apparatus for performing a diagnosis by using gamma radiation of a plurality of energies, the apparatus comprising:
a detector for detecting radiation;
a signal processing unit for acquiring information on an energy and a position from a signal of the detector;
an image creation unit for creating an image based on an energy corresponding to the gamma radiation of each of energies according to the data from the signal processing unit;
a three-dimensional image creation unit for creating a three-dimensional image for each of the energies from the images created for the respective energies by the image creation unit;
an image correction operation unit which performs a convolution on the three-dimensional image corresponding to the gamma radiation of the higher-energy side among the three-dimensional images created for the respective energies, wherein the convolution operation is executed by apply count values to be subtracted from a lower-energy side image to peripheral pixels of a pixel for which higher-energy gamma radiation is detected; and
a corrected image creation unit for subtracting the correction image from a three-dimensional image corresponding to the gamma radiation of the lower-energy side among the three-dimensional images created for respective energies by the image creation unit.

6. A nuclear medical diagnosis apparatus for performing a diagnosis by using gamma radiation of a plurality of energies, the apparatus comprising:
a detector for detecting the gamma rays;
a signal processing unit which outputs energy information and position information at respective detection points in the detector;
an image creation unit which creates a first image corresponding to the gamma radiation of the higher-energy side according to the energy information and the position information at the respective detection points from the signal processing unit and a second image corresponding to the gamma radiation of the lower-energy side;
an image correction operation unit which performs a convolution operation on the first image corresponding to the gamma radiation of the higher-energy side created by the image creation unit so as to create a third image corresponding to the gamma radiation of the higher-energy side to be superimposed on the second image corresponding to the gamma radiation of the lower-energy side, wherein the convolution operation is executed by applying count values to be subtracted from a lower-energy side image to peripheral pixels of a pixel for which higher-energy gamma radiation is detected; and
a corrected image creation unit which subtracts the third image corresponding to the gamma radiation of the higher-energy side to be superimposed, from the second image corresponding to the gamma radiation of the lower-energy side created by the image creation unit.

7. A nuclear medical diagnosis apparatus for performing a diagnosis by using gamma radiation of a plurality of energies, the apparatus comprising:
a detector for detecting the gamma radiation;
a signal processing unit which outputs energy information and position information at respective detection points in the detector;
an image creation unit which creates a first image corresponding to the gamma radiation of the higher-energy side according to the energy information and the position information at the respective detection points from the signal processing unit and a second image corresponding to the gamma radiation of the lower-energy side;
a first three-dimensional image creation unit which creates a three-dimensional image corresponding to the gamma radiation of the higher-energy side from the first image corresponding to the gamma radiation of the higher-energy side created by the image creation unit;
an image correction operation unit which performs a convolution operation on the three-dimensional image created by the three-dimensional image creation unit so as to create a third image corresponding to the gamma radiation of the higher-energy side to be superimposed on the second image corresponding to the gamma radiation of the lower-energy side, wherein the convolution operation is executed by applying count values to be subtracted from a lower-energy side image to peripheral pixels of a pixel for which higher-energy gamma radiation is detected;
a corrected image creation unit which subtracts the third image corresponding to the gamma radiation of the high-energy side to be superimposed, from the second image corresponding to the gamma radiation of the lower-energy side created by the image creation unit; and
a second three-dimensional image creation unit which creates a three-dimensional image corresponding to the gamma radiation of the lower-energy side from the image created by the subtraction in the corrected image creation unit.

8. An image processing method for a nuclear medical diagnosis apparatus for performing a diagnosis by using gamma radiation of a plurality of energies, the method comprising steps of:
detecting energy information and position information at a detection point upon detection of the gamma radiation;
creating a first image corresponding to the gamma radiation of the higher-energy side and a second image corresponding to the gamma radiation of the lower-energy side according to the energy information and the position information at the detection point of the detection;
performing a convolution operation on the first image corresponding to the gamma radiation of the higher-energy side on the first image corresponding to the gamma radiation of the higher-energy side so as to create a third image corresponding to the gamma radiation of the higher-energy side to be superimposed on the second image, wherein the convolution operation is executed by applying count values to be subtracted from a lower-energy side image to peripheral pixels of a pixel for which higher-energy gamma radiation is detected; and
subtracting the third image corresponding to the gamma radiation of the higher-energy side to be superimposed, from the second image corresponding to the gamma radiation of the lower-energy side.

* * * * *